(12) United States Patent
Schaefer

(10) Patent No.: US 7,491,326 B2
(45) Date of Patent: Feb. 17, 2009

(54) APPARATUS FOR DISTRIBUTING LIQUIDS HAVING AN ADAPTER

(75) Inventor: Uwe Schaefer, Keltern (DE)

(73) Assignee: Agilent Technologies, Inc., Santa Clara, CA (US)

( * ) Notice: Subject to any disclaimer, the term of this patent is extended or adjusted under 35 U.S.C. 154(b) by 571 days.

(21) Appl. No.: 11/207,217

(22) Filed: Aug. 19, 2005

(65) Prior Publication Data

US 2006/0219617 A1    Oct. 5, 2006

(30) Foreign Application Priority Data

Mar. 29, 2005    (EP) .................................. 05102451

(51) Int. Cl.
   *B01D 15/08* (2006.01)
(52) U.S. Cl. ...................... 210/198.2; 210/143; 422/70; 422/101
(58) Field of Classification Search ................. 210/656, 210/659, 143, 198.2; 422/70, 100, 101, 102
See application file for complete search history.

(56) References Cited

U.S. PATENT DOCUMENTS

| 3,765,461 | A | 10/1973 | Keck |
| 4,049,031 | A | 9/1977 | Cooper et al. |
| 6,197,198 | B1 * | 3/2001 | Messinger et al. .......... 210/656 |
| 6,355,164 | B1 * | 3/2002 | Wendell et al. .......... 210/198.2 |
| 6,406,633 | B1 * | 6/2002 | Fischer et al. ................ 210/659 |
| 6,562,232 | B2 * | 5/2003 | Myogadani ................... 210/94 |
| 6,627,075 | B1 * | 9/2003 | Weissgerber et al. ...... 210/198.2 |
| 6,936,167 | B2 * | 8/2005 | Hobbs et al. ............. 210/198.2 |
| 2002/0121468 | A1 | 9/2002 | Fischer et al. |
| 2004/0096986 | A1 | 5/2004 | Klein et al. |
| 2004/0237672 | A1 | 12/2004 | Jaeger |

FOREIGN PATENT DOCUMENTS

GB            995016            6/1965

* cited by examiner

*Primary Examiner*—Ernest G Therkorn
(74) *Attorney, Agent, or Firm*—Marc Bobys

(57) ABSTRACT

An apparatus for distributing liquids to one or more receiving elements. The apparatus comprises a first element arrangement having one or more first receiving elements, a second element arrangement having one or more second receiving elements, a distributor adapted for distributing liquids to the first receiving elements, and an adapter adapted for transferring the liquids from the first receiving elements to the second receiving elements.

23 Claims, 5 Drawing Sheets

APPARATUS FOR DISTRIBUTING LIQUIDS HAVING AN ADAPTER

FIELD OF THE INVENTION

The present invention relates to an apparatus for distributing liquids to one or more receiving elements.

DISCUSSION OF THE BACKGROUND ART

The field of laboratory technology, in particular of microfluidic laboratory technology, comprises chemical, physical and/or biological analysis, separation, synthesis or preparation of substances, in particular of compounds or fractions of a liquid. Such laboratory technology may comprise liquid chromatography using liquid chromatographic columns. Components or fractions may be collected as they elute from LC columns and subjected to further analysis as for example, by mass spectrometry. In order to collect the components or fractions a fraction collecting apparatus is used. Such a fraction collector is adapted to collect the fractions or components within several collection vessels or containers. To this end such a fraction collector comprises a distributing device or distributor adapted for distributing the respective fractions or compounds to the vessels or containers. An example of a fraction collecting system is disclosed in US 2002/0121468 A1.

SUMMARY OF THE INVENTION

It is an object of the invention to provide an improved handling of such a distributing apparatus, and in particular, to provide improved flexibility with respect to collecting fractions or components having different volumes. This object is solved as described in the independent claims. Preferred embodiments are shown by the dependent claims.

According to embodiments of the invention the objective indicated are achieved by providing the apparatus with an adapter, said adapter is adapted for transferring liquids from first receiving elements to second receiving elements. The first receiving elements are arranged within a first element arrangement. The second receiving elements are arranged in a second element arrangement. The apparatus also comprises a distributor adapted for distributing liquids to the first receiving elements. Since such a distributor is limited in distributing the liquids only to the first receiving elements, the size of such first receiving elements is restricted. If the first receiving elements are designed as containers, such containers will have only very small collecting capacities, for example in the range of several milliliters. With help of the adapter the first receiving elements are coupled to the second receiving elements which do not depend on the restrictions of the distributor. Therefore, the second receiving elements can be provided with larger collecting capacities than the first receiving elements, e.g. in the range of centiliters, when the second receiving elements are designed as containers or vessels. According to this embodiments of the invention the collecting of larger quantities of liquid, for example fractions or compounds is provided.

According to another embodiment the adapter comprises a fitting arrangement having one or more fittings. Preferably, at least one of said fittings is adapted for aligning a transfer line to an opening of a single second receiving element. Particularly, at least one of said transfer lines is adapted to transfer a liquid from a single first receiving element to a single second receiving element. Preferably, another embodiment comprises for each pair of first receiving element and second receiving element a transfer line and a fitting. Consequently, the adapter provides an appropriate correlation between the first and second receiving elements.

According to other embodiments the adapter may comprise a fitting support adapted for supporting the fittings of the fitting arrangement. Said fitting support preferably comprises a fixed plate adapted for receiving the fittings and a moveable plate adapted for securing the fittings to the fitting support. The fixed plate may contain one or more receiving openings each adapted for receiving a single fitting, wherein said receiving openings and said fittings preferably are adapted for becoming adjusted into a predetermined position. Said predetermined positions are arranged relative to the second element arrangement in order to optimize the alignment of the transfer lines to the openings of the second receiving elements, said alignment being achieved by shape of the fittings. Additionally, the moveable plate may contain one or more locking openings each adapted for receiving a single fitting, wherein the locking openings and the fittings preferably are adapted to establish a form-fit locking between the moveable plate and the fittings. By means of such a form-fit locking the fittings are secured to the fitting support and cannot be extracted by mistake. Therefore, the fitting support improves the reliability of the apparatus.

Embodiments also relate to a fluid separation system adapted for separating compounds of a fluid. Said system comprises the aforementioned apparatus and at least a fluid providing unit and a separation unit adapted for separating compounds of the fluid and an arrangement of at least one separation column. Since the apparatus allows the collecting of large quantities of separated fluids or liquids the field of application of such a system can be expanded.

BRIEF DESCRIPTION OF DRAWINGS

Many other advantages of embodiments of the present invention will be readily appreciated and become better understood by reference to the following more detailed description of embodiments in connection with the accompanied drawings. Features that are substantially or functionally equal or similar will be referred to by the same reference signs.

DETAILED DESCRIPTION OF THE PREFERRED EMBODIMENT

Figure 1:
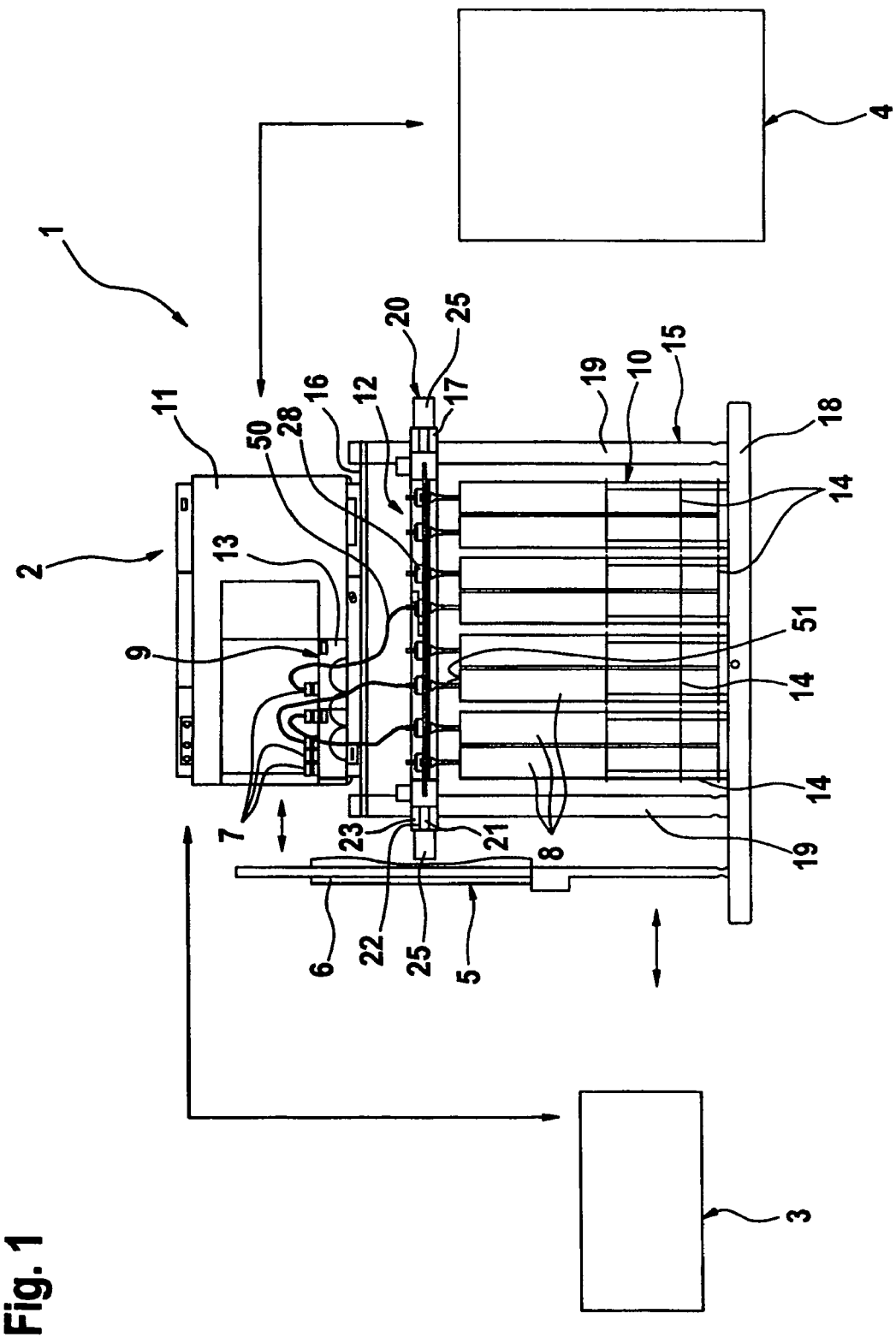
FIG. 1 depicts a simplified schematic view of a fluid separation system, according to embodiments of the invention.

According to FIG. 1 a fluid separation system 1 comprises a distributing apparatus 2 and at least one of a fluid provider 3, a separation unit 4 and a column arrangement 5. The system 1 in general is adapted for separating compounds of a fluid and is usually used in the field of laboratory fluid processing, in particular for analytical or preparative purposes. The fluid provider 3 is adapted for providing the respective fluid, which is preferably a liquid but also may be a gas. The fluid provider 3 may comprise a nano-pump in particular a nano-pump disclosed in U.S. Pat. No. 6,627,075 B1, which is incorporated herein by reference. The provider 3 is coupled to the apparatus 2 and to the column arrangement 5.

The separation unit 4 is adapted for separating compounds of the fluid. Preferably, the separation unit 4 comprises or is a chromatography system, in particular a liquid chromatography system. As for example high performance liquid chromatography systems. HPLC is a form of chromatography used to separate compounds, that are dissolved in liquid. The separation unit 4 is coupled to the apparatus 2.

The column arrangement 5 comprises at least one separation column 6. Such separation columns 6 usually are adapted for providing a compound specific retention, i.e. such a separation column 6 is provided different retentions different compounds. Thus, the separation column 6 provides a compound specific retardation within a liquid flowing through the separation column 6, said retardation results in a separation of the different compounds. Accordingly, the liquid flowing out of the separation column 6 contains the separated compounds consecutively such that portions of the liquid containing the respective compounds be separated. The column arrangement 5 is coupled to the apparatus 2.

Each of said couplings is symbolized by a double-arrow.

The apparatus 2 is adapted for distributing liquids to one or more or preferably to several receiving elements 7, 8. The apparatus 8 comprises a first element arrangement 9, comprising one or more or preferably several first receiving elements 7. The distributor 11 preferably is adapted for supporting the first element arrangement.

According to FIGS. 1 und 2 the apparatus 2 also comprises a second element arrangement 10 comprising one or more or preferably several second receiving elements 8. Further the apparatus 2 comprises a distributor 11 adapted for distributing liquids to the first receiving elements 7. Such a distributor 11 may be of the type of Fraction Collector of the Agilent 1100 Series G1364A by the applicant Agilent Technologies.

The apparatus 2 furthermore is provided with an adapter 12. Said adapter 12 is adapted for transferring the liquids from the first receiving elements 7 to the second receiving elements 8.

The apparatus 2 preferably is designed as a fraction collector. Such a fraction collector is adapted for analytical and/or preparative handling fluid fraction. Such a fraction collector is preferably used in the field of liquid chromatography.

Figure 2:
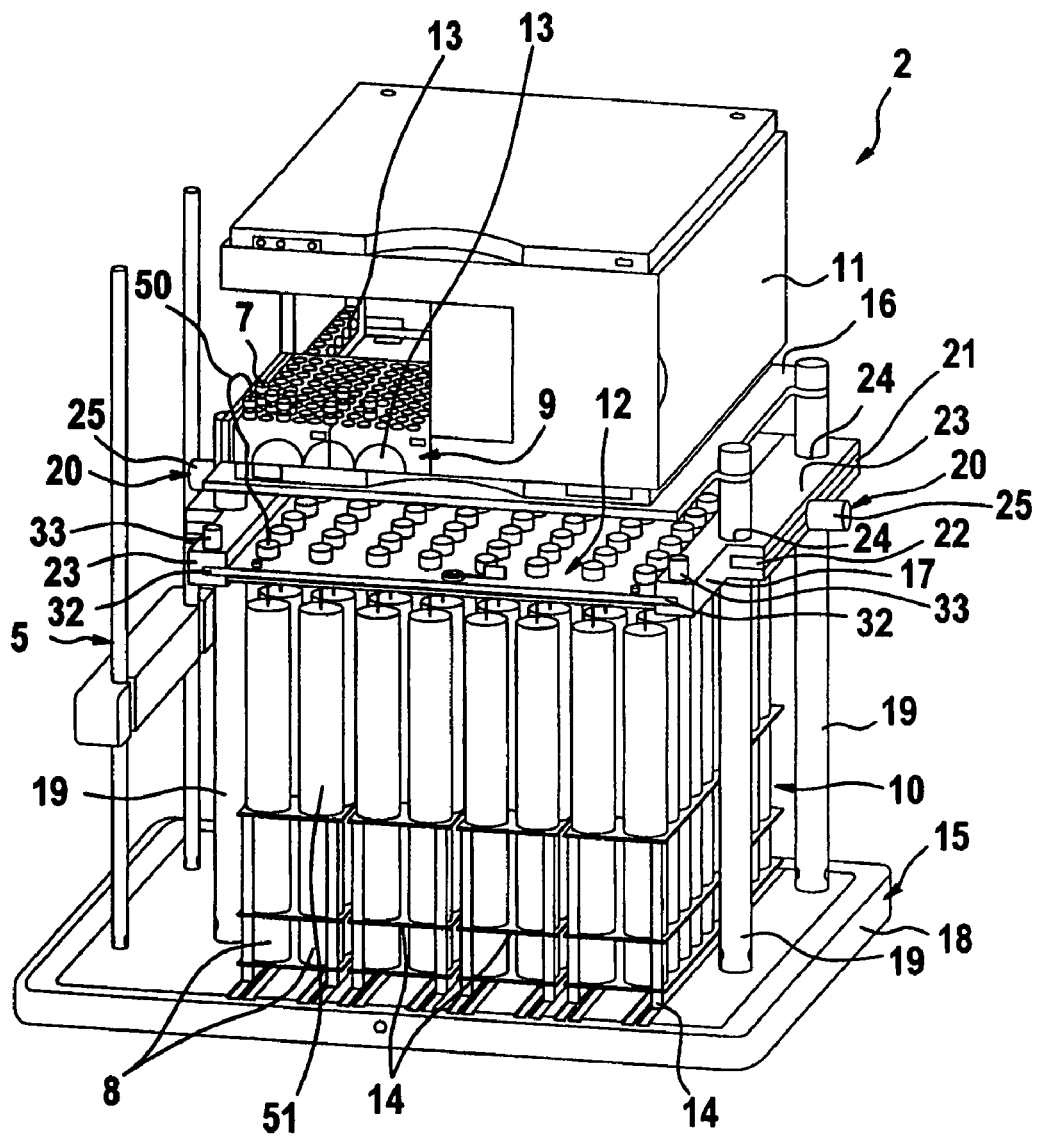
FIG. 2 depicts a perspective view of an apparatus according to embodiments of the invention.
Figure 3:
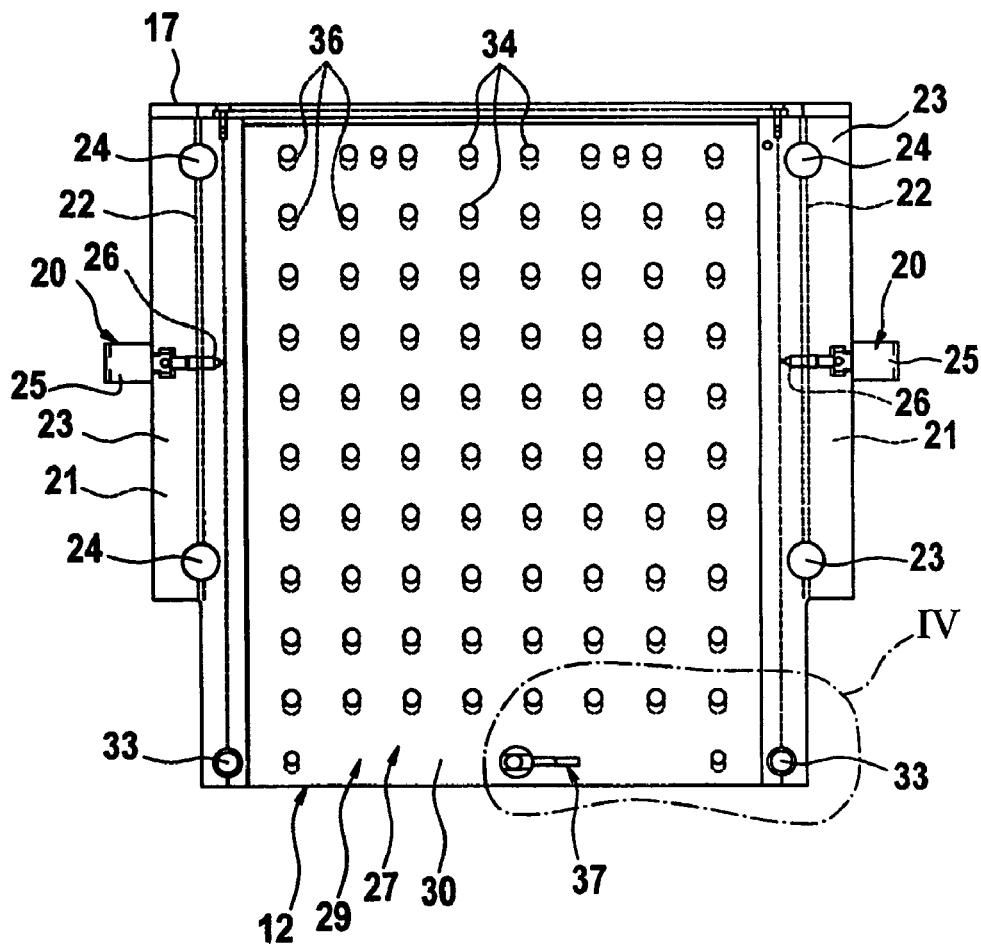
FIG. 3 depicts a top view of a mid-level platform of the apparatus.

In order to simplify the handling of the apparatus 2 the first element arrangement 9 comprises in a preferred embodiment at least one first positioning cage 13. In the embodiment depicted in the FIGS. 1 and 2 the first element arrangement 9 comprises two first positioning cages 13. Each first positioning cage 13 is adapted for positioning one or more or in particular several first receiving elements 7 in fact in predetermined positions relative to each other. The first receiving elements 7 may be designed as first containers or first vessels adapted for collecting a liquid. In such an embodiment said first containers have a relative small collection capacity, e.g. in the range of several milliliters.

The second element arrangement 10 preferably comprises at least one second positioning cage 14. In the depicted embodiment the second element arrangement 10 comprises four second positioning cages 14. Each second positioning cage 14 is adapted for positioning one or more or preferably several second receiving elements 8 in fact in predetermined positions relative to each other. By means of that second positioning cages 14 the handling of the second receiving elements 8 and therefore the handling of the apparatus 2 is simplified. The second receiving elements 8 preferably are designed as second containers or vessels adapted for collecting a liquid. In the depicted embodiment the second receiving elements 8 are designed as test-tubes. The second receiving elements 8 or second containers, respectively, have larger collecting capacities than the first receiving elements 7 or first containers, respectively. Preferably, the second containers have collecting capacities in the range of centiliters.

According to a preferred embodiment each first receiving element 7 is assigned to a single second receiving element 8 and vice versa. That means, that the number of first receiving elements 7 is equal to the number of the second receiving elements 8, and that every single first receiving element 7 has one corresponding second receiving element 8. Accordingly, the adapter 12 is adapted for transferring the liquids from every first receiving element 7 to each respective second receiving element 8.

The apparatus 2 is also provided with a rack 15. Said rack 15 is adapted for supporting the distributor 11, the adapter 12 and the second element arrangement 10. The rack 15 comprises in the preferred embodiment according to FIGS. 1 and 2 a upper-level platform 16, a mid-level platform 17 and a low-level platform 18. The upper-level platform 16 is adapted for supporting the distributor 11. The mid-level platform 17 is adapted for supporting the adapter 12 and the low-level platform 18 is adapted for supporting the second element arrangement 10. The low-level platform 18 is also designed as a base plate adapted for supporting the whole rack 15.

The rack 15 comprises also several rods 19 supported by the low-level platform 18 and supporting the upper-level platform 16. The mid-level platform 17 is attached to the rods 19 between the low-level platform 18 and the upper-level platform 16. The rack 15 preferably is adapted for adjusting the level of the mid-level platform 17 relative to the low-level platform 18 and the upper-level platform 16. To this end the mid-level platform 17 is provided with an adjustment device 20. That adjustment device 20 comprises in the shown embodiment a clamping bar 21 which is slideably arranged within a slot 22 of a carrier 23. Said carrier 23 is provided with at least one through hole 24, through which one of the rods 19 extends. Each of this through holes 24 is open to the slot 22. The adjusting device 22 also comprises a fixation screw 25. Said fixation screw 25 is rotateably supported at the clamping bar 21, penetrates the clamping bar 21 and extends into a thread hole 26. Said thread hole 26 is provided at the carrier 23 and is open to the slot 22. Tightening of the fixation screw 25 forces the clamping bar 21 into the slot 22 and against the rod 19. Accordingly, the respective rod 19 is clamped within the respective through hole 24 between the carrier 23 and the clamping bar 21.

In order to adjust the level of the mid-level platform 17 the fixation screw 25 is loosened. Accordingly, the carrier 23 and therefore the mid-level platform 17 are adjustable along the rods 19. The adjusting device 20 comprises in the depicted embodiment to arrangements of carrier 23, clamping bar 21 and fixation screw 25, each arrangement assigned to a side of the rack 15 provided with at least one rod 19.

According to the FIGS. 2 to 7 the adapter 12 comprises a fitting arrangement 27 comprising one or more or preferably several fittings 28. In the FIGS. 3 and 4 the fittings 28 are not shown. The adapter 12 also comprises a fitting support 29 adapted for supporting the fitting arrangement 27 or the fittings 28 of the fitting arrangement 27, respectively. Said fitting support 29 comprises a fixed plate 30 and a moveable plate 31, see FIGS. 6 and 7. The fixed plate 30 is adapted for receiving the fittings 28 and is supported by the mid-level platform 17. To this end the fixed plate 30 is at two opposing edges inserted into receiving slots 32 provided at the carriers 23 of the adjustment device 20. The fixed plate 30 is secured to said carriers 23 by means of clamping screws 33. The tightened clamping screws 33 press the fixed plate 30 against the carrier 23 within the receiving slot 32.

The fixed plate 30 contains or more or preferably several receiving openings 34 each adapted for receiving a single fitting 28. In order to adjust a predetermined relative position of the respective fittings 28 the receiving openings 34 and the fittings 28 interact accordingly. The receiving openings 34 are adapted to the second element arrangement and define said predetermined relative positions of the fittings 28.

The moveable plate 31 is moveably attached to the fixed plate 30. The moveable plate 31 is adapted to perform movements, preferably translatory movements, relative to the fixed plate 30. Said movements are symbolized in FIG. 7 by means of a double-arrow 35. Further the moveable plate 31 is adapted for securing the fittings 28 to the fitting support 29. To this end, the moveable plate 31 contains one or more or preferably several locking openings 36 each adapted for receiving a single fitting 28. In order to establish a form-fit locking between the moveable plate 31 and the fittings 28 the locking openings 36 and the fittings 28 interact accordingly. Said form-fit locking is preferably adapted to prevent extracting of the fittings 28 from the fitting support 29 or out of the locking openings 36 and the receiving openings 34, respectively. According to the depicted preferred embodiment the moveable plate 31 is arranged underneath the fixed plate 30. It should be clear, that in another embodiment the fixed plate 30 could be arranged underneath the moveable plate 31.

In order to perform the movement 35 between the plates 30, 31 the fitting support 29 comprises at least one excenter drive 37. Said excenter drive 37 is adapted for providing said movement 35 of the moveable plate 31 relative to the fixed plate 30. To this end the excenter drive 37 is pivotably supported at the one of the plates, here at the fixed plate 30. The excenter drive 37 comprises a cylinder 38 inserted into a bearing opening 39, which is provided at the fixed plate 30. Said cylinder 38 is coupled with a lever 40 adapted for providing a handling of the excenter drive 37. The cylinder 38 is pivotably seated within the bearing opening 39 with respect to a rotation axis 41.

Figure 4:
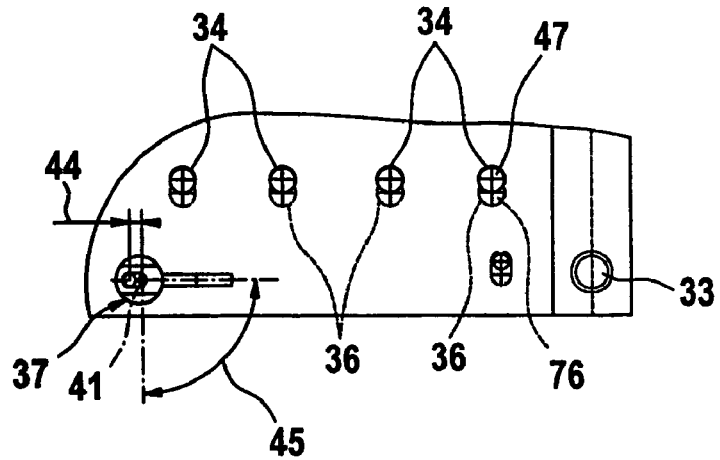
FIG. 4 depicts an enlarged detail IV of FIG. 3.
Figure 5:
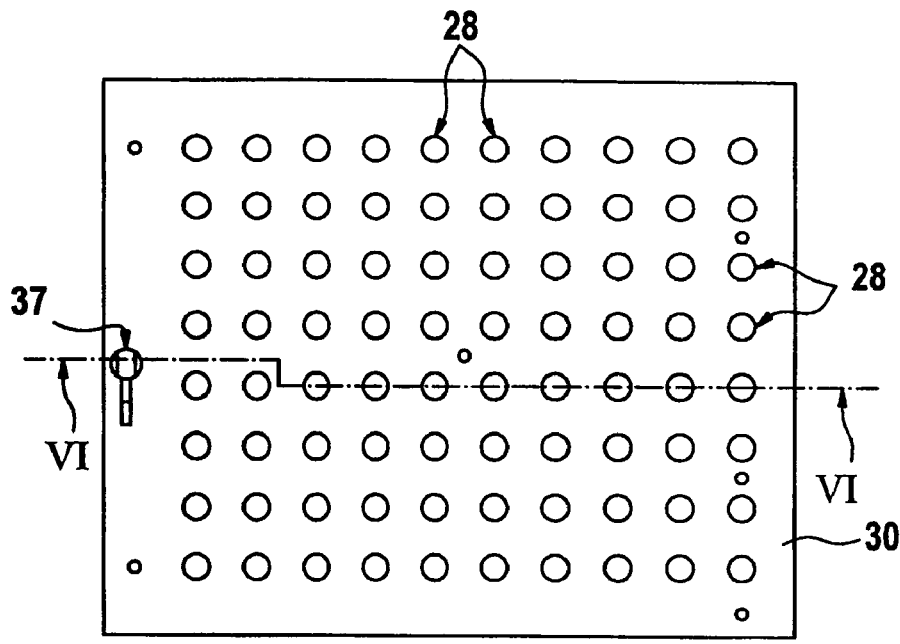
FIG. 5 depicts a top view of a fitting support of the apparatus.
Figure 6:
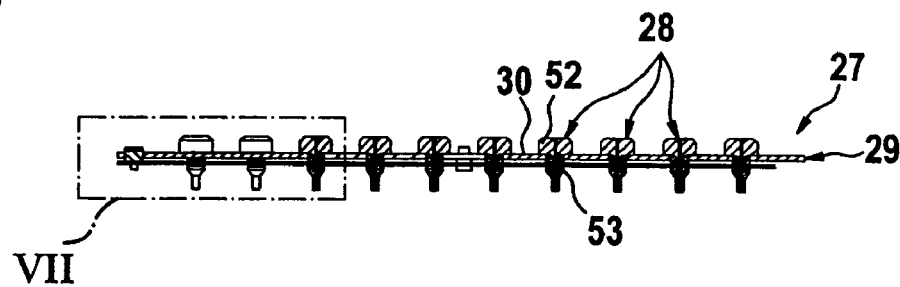
FIG. 6 depicts a cross section according to section lines VI in FIG. 5.

The excenter drive 37 or its cylinder 38, respectively, is also provided within an excenter pin 42 extending into a drive slot 43 provided at the other of the plates, here at the moveable plate 31. The excenter pin 42 is arranged eccentrically with respect to the rotation axis 41. An eccentricity 44 between the rotation axis 41 and the excenter pin 42 is depicted in FIG. 4.

The excenter drive 37 is adjustable between a release position and a locking position. In the depicted embodiment the excenter drive 37 is adjusted in its locking position. Said locking position is adapted for securing the inserted fittings 38 to the fitting support 29. In order to adjust the release position the cylinder 38 has to be turned around the rotation axis 41 by a predetermined angle 45. Said angle 45 is for example 90°. The release position is adapted for inserting and extracting the fittings 28 into or from the fitting support 29.

In order to perform the locking function and the release function of the moveable plate 31 the locking openings 36 preferably are provided with a cross-section having the shape of a key hole or a wedge or a triangle. According to FIG. 4 said cross-section has a release portion 46 having at least the diameter of the respective receiving opening 34. In the release position the receiving openings 34 are aligned to the receiving portions 46 of the respective locking openings 36. Accordingly the fittings 28 can be inserted or extracted, respectively.

The cross-section of each locking opening 36 also has a locking portion 47 characterized by a reduced diameter. In the locking position the receiving openings 34 are aligned to the locking portions 47 of the respective locking openings 36.

In order to perform the form-fit locking between the moveable plate 31 and the fittings 28 each fitting 28 is provided with a locking portion 48 adapted for interacting with the respective locking opening 26. Said locking portion 48 of the fitting 28 is characterized by a cross-section, which is smaller than the cross-section of adjacent portions of the fitting 28 on both sides of the locking portion 48. Accordingly, the locking portion 47 of the locking opening 36 engages with the locking portion 48 of the fitting 28, when the moveable plate 31 is adjusted in the locking position.

The fittings 28 are also provided with a positioning portion 49 adapted for interacting with the respective receiving opening 34. Preferably the receiving opening 34 and the receiving portions 49 have approximately the same diameter and are preferably adapted for providing only a small clearance.

Figure 7:
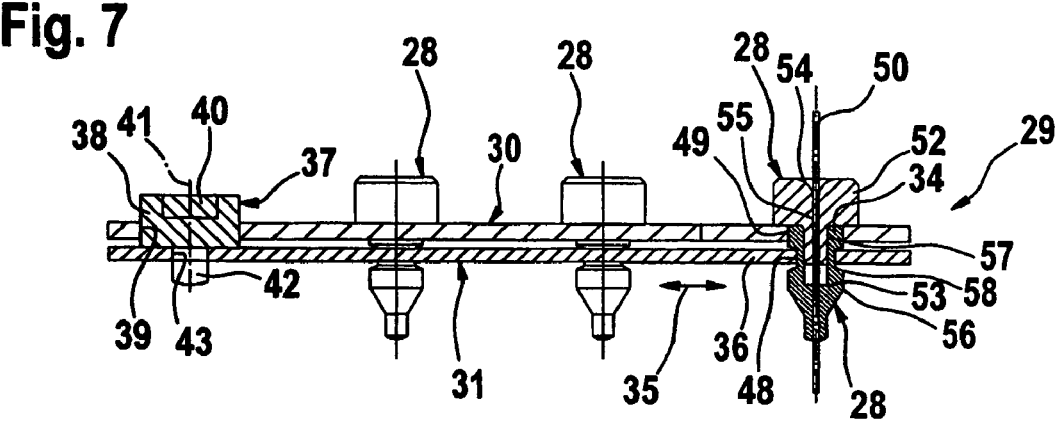
FIG. 7 depicts an enlarged detail VII in FIG. 6.

According to FIG. 7 the fittings 28 are adapted for aligning a transfer line 50 with respect to an opening 51 of a single second receiving element 8. Said transfer line 50 is, for example, provided by means of flexible hose or tube. Each transfer line 50 is coupled to a single first receiving element 7. Accordingly, each fitting 28 is assigned to a single first receiving element 7 and to a single second receiving element 8. Said transfer line 50 is adapted to transfer a liquid from a single first receiving element 7 to a single second receiving element 8.

Each fitting 28 comprises an insert member 52 and an alignment member 53. The insert member 52 is adapted for inserting the transfer line 50 into the fitting 28. To this end the insert member 52 is provided with a funneled insert opening 54 and a center bore 55. The alignment member 53 is adapted for aligning the transfer line 50 to the opening 51 of the respective second receiving element 8. To this end the alignment member 53 is provided with a center bore 56 aligned to the center bore 55 of the insert member 52. The transfer line 50 extends out of the alignment member 53 and ends approximately at the level of the respective opening 51. The insert member 52 and the alignment member 53 are joint together for example by means of a thread connection 57.

Insert member 52 and alignment member 53 are adapted for interacting in order to fix the transfer line 50 to the respective fitting 28. To this end at least one fixing member 58 is axially arranged between a portion of the insert member 52 and a portion of the alignment member 53. Said fixing member 58 encloses the transfer line 50 and is made of an elastic material, for example plastics or synthetics. Preferably the fixing member 58 is a O-ring seal. Said fixing member 58 is axially compressed, when the insert member 52 is joined to the alignment member 53. As a result of said axial compression the fixing member 58 extends radially and accordingly compresses the transfer line 50 in order to establish a suitable fixation of the transfer line 50 to the fitting 28.

Figure 8:
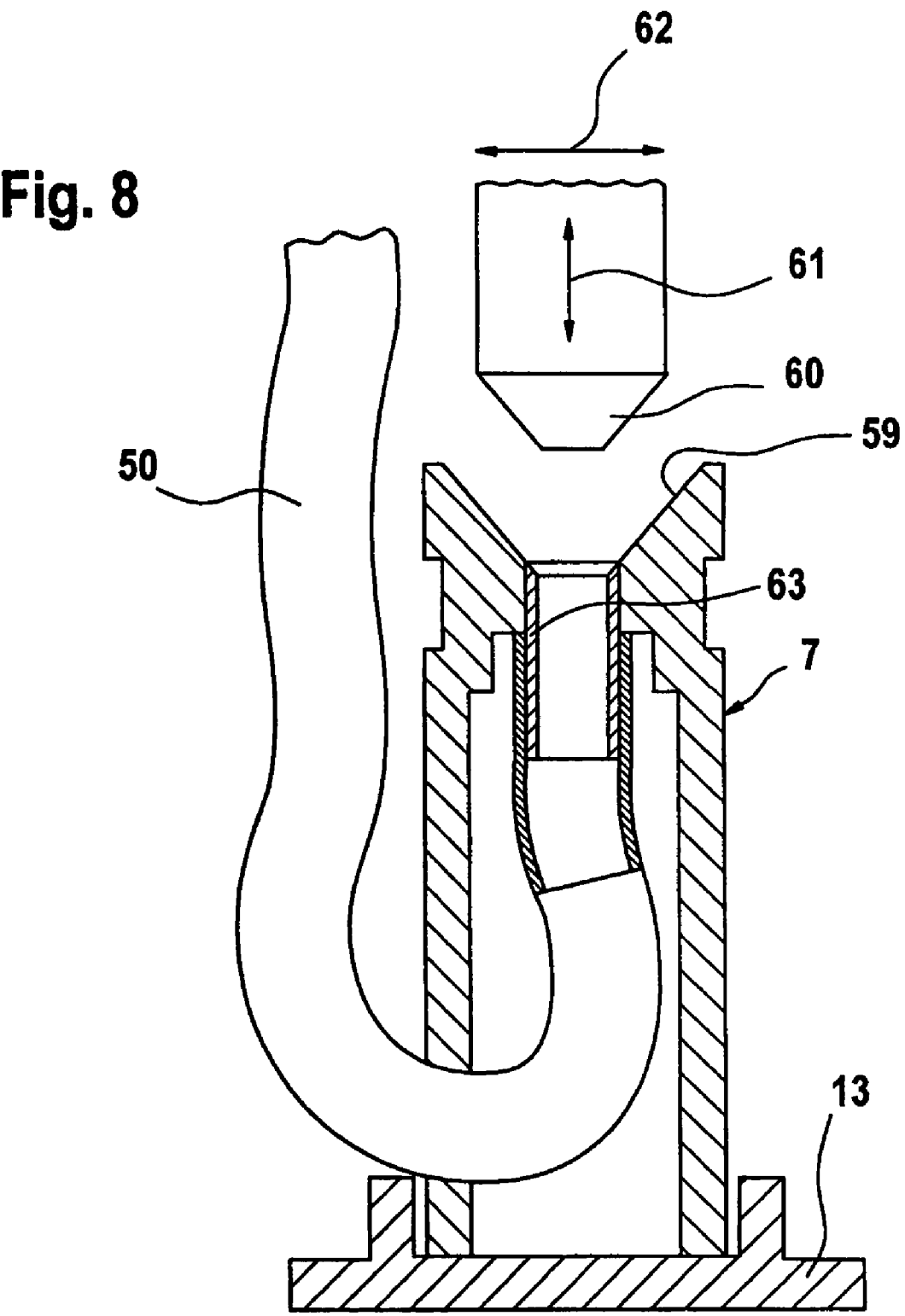
FIG. 8 depicts a simplified cross section of a first receiving element of the apparatus.

Preferring now to FIG. 8 at least one of the first receiving elements 7 comprises in a preferred embodiment an inlet port 59. The distributor 11 is provided with an outlet port 60 which is moveable vertically and horizontally in order to distribute the liquid to the different first receiving elements 7 of the first element arrangement 9.

The inlet port 59 is adapted for interacting with the outlet port 60, for example the inlet port 59 and/or the outlet port 60 has/have a conus shape. Accordingly, the inlet port 59 defines a seating for the outlet port 60, said seating establishes a pressure tight coupling between inlet port 59 and outlet port 60. Accordingly, the distributor 11 may be adapted for injecting the respective liquid pressurized out of its outlet port 60 and therefore into the inlet port 59 and thus into the respective first receiving element 7.

The inlet port 59 is coupled to a connecting sleeve 63. Said connecting sleeve 63 is coupled to the transfer line 50.

The adapter 12 allows collecting of larger quantities of liquids by using a conventional distributor 11 adapted for distributing the liquids to the first receiving elements 7 provided with small collecting capacities, since the adapter 12 transfers the liquids from the first receiving elements 7 to the larger second receiving elements 8.

What is claimed is:

1. A fluid separation system adapted for separating compounds of a fluid, comprising: an apparatus for distributing liquids to one or more receiving elements, comprising: a first element arrangement having one or more first receiving elements, a second element arrangement having one or more second receiving elements, a distributor adapted for distributing liquids to the first receiving elements, and an adapter adapted for transferring the liquids from the first receiving elements to the second receiving elements, wherein: the adapter comprises a fitting arrangement having one or more fittings, the adapter comprises a fitting support adapted for supporting the fittings of the fitting arrangement, and the fitting support comprises a moveable plate adapted for securing the fittings to the fitting support; and at least one of the following features a fluid provider adapted for providing the fluid, a separation unit adapted for separating compounds of the fluid, an arrangement of at least one separation column.

2. The fluid separation system according to claim 1, comprising at least one of the features: the first element arrangement comprises at least one first positioning cage adapted for positioning one or more first receiving elements in predetermined positions relative to each other, the second element arrangement comprises at least one second positioning cage adapted for positioning one or more second receiving elements in predetermined positions relative to each other; the second containers have larger collecting capacities than the first containers.

3. The fluid separation system according to claim 1, comprising at least one of the features: each second receiving element is assigned to a single first receiving element an vice versa, at least one first receiving element is designed as a first container adapted for collecting a liquid, at least one second receiving element is designed as a second container adapted for collecting a liquid.

4. The fluid separation system according to claim 1, wherein the apparatus comprises a rack adapted for supporting the distributor, the adapter and the second element arrangement.

5. The fluid separation system according to claim 4, comprising at least one of the features: the rack comprises a upper-level platform adapted for supporting the distributor, the rack comprises a mid-level platform adapted for supporting the adapter, the rack comprises a low-level platform adapted for supporting the second element arrangement, the rack is adapted for adjusting the level of the mid-level platform relative to at least one of the low-level platform and the upper-level platform, the mid-level platform is with respect to the direction of gravity arranged between the low-level platform and the upper-level platform.

6. The fluid separation system according to claim 1, comprising at least one of the features: at least one fitting is adapted for aligning a transfer line to an opening of a single second receiving element, at least one transfer line is adapted to transfer a liquid from a single first receiving element to a single second receiving element, at least one transfer line is provided by means of a flexible hose or tube, each transfer line is coupled to a single first receiving element.

7. The fluid separation system according to claim 1, comprising at least one of the features: each fitting is assigned to a single first receiving element and to a single second receiving element, at least one fitting comprises an insert member adapted for inserting the transfer line into the fitting, at least one fitting comprises an alignment member adapted for aligning the transfer line to the opening of the respective second receiving element.

8. The fluid separation system according to claim 1, comprising at least one of the features: the insert member and the alignment member of at least one fitting are adapted for interacting in order to fix the transfer line to the fitting, at least one first receiving element comprises an inlet port adapted for interacting with an outlet port of the distributor, the inlet port of at least one first receiving element is coupled to a transfer line, the inlet port of at least one first receiving element and the outlet port are adapted for establishing a pressure-tight coupling.

9. The fluid separation system according to claim 1, comprising at least one of the features: at least one transfer line is adapted for transferring a liquid to a single second receiving element, at least one transfer line is designed as a flexible hose or a tube.

10. The fluid separation system according to claim 1, wherein the distributor is adapted to inject the respective liquid pressurized into the respective first receiving element through its outlet port.

11. The fluid separation system according to claim 1, wherein the fitting support comprises a fixed plate adapted for receiving the fittings.

12. The fluid separation system according to claim 1, wherein the moveable plate is adapted to perform movements, in particular translatory movements, relative to the fixed plate.

13. The fluid separation system according to claim 1, wherein the fixed plate contains one or more receiving openings each adapted for receiving a single fitting.

14. The fluid separation system according to claim 1, wherein the receiving openings and the fittings are adapted for interacting in order to adjust predetermined relative positions of the fittings.

15. The fluid separation system according to claim 1, wherein the moveable plate contains one or more locking openings each adapted for receiving a single fitting.

16. The fluid separation system according to claim 1, wherein the locking openings and the fittings are adapted for interacting in order to establish a form-fit locking between the moveable plate and the fittings.

17. The fluid separation system according to claim 1, wherein the form-fit locking is adapted to prevent extracting of the fittings from the fitting support.

18. The fluid separation system according to claim 1, wherein the moveable plate is arranged underneath the fixed plate.

19. The fluid separation system according to claim 1, wherein at least one locking opening is provided with a cross section having the shape of at least one of a keyhole, a wedge and a triangle, at least one fitting is provided with a positioning portion adapted for interacting with the respective receiving opening, at least one fitting is provided with a locking portion adapted for interacting with the respective locking opening.

20. The fluid separation system according to claim 1, wherein the locking portion of at least one fitting has a cross section, which is smaller than the cross section of adjacent portions of the fitting on both sides of the locking portion.

21. The fluid separation system according to claim 1, wherein the fitting support comprises at least one excenter drive adapted for providing a movement of the moveable plate relative to the fixed plate.

22. The fluid separation system according to claim 21, comprising at least one of the features: the excenter drive is pivotably supported at the one of the plates and is provided with an excenter pin extending into a drive slot provided at the other of the plates, the excenter drive is adjustable between a release position adapted for inserting and extracting the fittings and a locking position adapted for securing the inserted fittings.

23. The fluid separation system according to claim 1, wherein the apparatus is designed as a fraction collector adapted to perform analytical and/or preparative handling of fluids, in particular in liquid chromatography.

* * * * *

UNITED STATES PATENT AND TRADEMARK OFFICE
CERTIFICATE OF CORRECTION

PATENT NO. : 7,491,326 B2 Page 1 of 1
APPLICATION NO. : 11/207217
DATED : February 17, 2009
INVENTOR(S) : Uwe Schaefer It is certified that error appears in the above-identified patent and that said Letters Patent is hereby corrected as shown below:

In column 7, line 42, in Claim 3, delete "an" and insert -- and --, therefor.

Signed and Sealed this

Twenty-third Day of June, 2009

JOHN DOLL
*Acting Director of the United States Patent and Trademark Office*